United States Patent [19]

Eberlein et al.

[11] 4,424,226

[45] Jan. 3, 1984

[54] PYRIDOBENZODIAZEPINONES, PHARMACEUTICAL COMPOSITIONS THEREOF AND METHOD OF USE THEREOF

[75] Inventors: Wolfgang Eberlein, Biberach; Günter Trummlitz, Warthausen; Günther Schmidt; Wolfhard Engel, both of Biberach, all of Fed. Rep. of Germany; Rudolf Hammer, Milan; Piero Del Soldato, Monza, both of Italy

[73] Assignee: Dr. Karl Thomae GmbH, Biberach an der Riss, Fed. Rep. of Germany

[21] Appl. No.: 462,377

[22] Filed: Jan. 31, 1983

[30] Foreign Application Priority Data

Feb. 9, 1982 [DE] Fed. Rep. of Germany ....... 3204403

[51] Int. Cl.³ ..................... A61K 31/55; C07D 471/04
[52] U.S. Cl. ................................. 424/263; 424/256; 424/267; 260/239.3 T
[58] Field of Search ................. 260/239.3 T; 424/267, 424/263, 256

[56] References Cited

U.S. PATENT DOCUMENTS 4,377,576 3/1983 Schmidt et al. .............. 260/239.3 T Primary Examiner—Robert T. Bond
Attorney, Agent, or Firm—Hammond & Littell, Weissenberger & Muserlian

[57] ABSTRACT

This invention relates to compounds of the formula

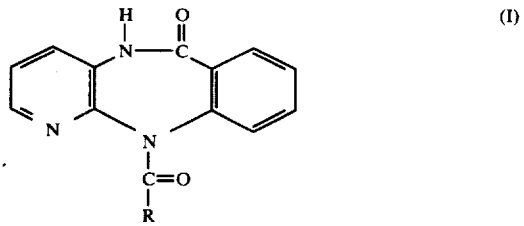

(I)

wherein R is (1-methyl-4-piperidinyl)methyl, (1-methyl-1,2,5,6-tetrahydro-4-pyridinyl)methyl, 1-methyl-1,2,5,6-tetrahydro-4-pyridinyl, (1-methyl-4-piperidinylidene)-methyl, 2,3-dehydro-8-methyl-8-azabicyclo[3.2.1]oct-3-yl methyl, endo-8-methyl-8-azabicyclo[3.2.1]oct-3-yl-methyl, or exo-8-methyl-8-azabicyclo[3.2.1]oct-3-yl-methyl, each of which may optionally have one or two methyl substituents on the six-membered heterocyclic ring, and non-toxic, pharmacologically acceptable acid addition salts thereof. The compounds as well as their salts are useful as anti-ulcerogenics.

6 Claims, No Drawings

PYRIDOBENZODIAZEPINONES, PHARMACEUTICAL COMPOSITIONS THEREOF AND METHOD OF USE THEREOF

FIELD OF THE INVENTION

This invention relates to novel pyridobenzodiazepinones. More particularly, this invention relates to novel pyridobenzodiazepinones and non-toxic acid addition salts thereof, methods of preparing these compounds, pharmaceutical compositions containing them as active ingredients, and a method of using them as anti-ulcerogenics and gastric acid secretion inhibitors.

BACKGROUND OF THE INVENTION

Pyridobenzodiazepinones with anti-ulcerogenic and secretion-inhibiting properties are known. Such compounds are described, for example, in U.S. Pat. Nos. 3,660,380, 3,691,159, 4,210,648, 4,213,984, and 4,213,985. However, pyridobenzodiazepinone compounds have now been found which have valuable pharmacological properties superior to those of the previously known compounds.

OBJECTS OF THE INVENTION

It is an object of the invention to provide novel pyridobenzodiazepinones having useful pharmacodynamic properties superior to those of the related compounds disclosed in the prior art.

It is also an object of the invention to provide pharmaceutical compositions containing pyridobenzodiazepinones as active ingredients.

It is a further object of the invention to provide a method of using substituted pyridobenzodiazepinones as anti-ulcerogenics and gastric acid secretion inhibitors.

These and other objects of the invention will become more apparent from the discussion below.

DETAILED DESCRIPTION OF THE INVENTION

The present invention relates to a novel class of pyridobenzodiazepinones represented by the formula

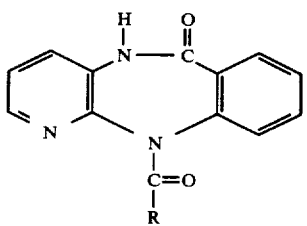

wherein R is (1-methyl-4-piperidinyl)methyl, (1-methyl-1,2,5,6-tetrahydro-4-pyridinyl)methyl, 1-methyl-1,2,5,6-tetrahydro-4-pyridinyl, (1-methyl-4-piperidinylidene)-methyl, (2,3-dehydro-8-methyl-8-azabicyclo[3.2.1]oct-3-yl)methyl, or endo- or exo-(8-methyl-8-azabicyclo[3.2.1]oct-3-yl)methyl, each of which may optionally have one or two methyl substituents on the six-membered heterocyclic ring, or non-toxic, pharmaceutically acceptable acid addition salts thereof.

The compounds of Formula I may be obtained in the form of their non-toxic, pharmacologically acceptable salts after reaction with inorganic or organic acids. Suitable acids include, for example, hydrochloric, hydrobromic, sulfuric, methylsulfuric, phosphoric, tartaric, fumaric, citric, maleic, succinic, gluconic, malic, p-toluenesulfonic, methanesulfonic, and amidosulfonic acid.

The following compounds are illustrative of the invention:

(a) 5,11-dihydro-11-[(1-methyl-4-piperidinyl)acetyl]-6H-pyrido[2,3-b][1,4]benzodiazepin-6-one;
(b) 5,11-dihydro-11-[(1,3-dimethyl-4-piperidinyl)acetyl]-6H-pyrido[2,3-b][1,4]benzodiazepin-6-one;
(c) 5,11-dihydro-11-[(1,2-dimethyl-4-piperidinyl)acetyl]-6H-pyrido[2,3-b][1,4]benzodiazepin-6-one;
(d) cis-5,11-dihydro-11-[(1,2-dimethyl-4-piperidinyl)acetyl]-6H-pyrido[2,3-b][1,4]benzodiazepin-6-one;
(e) trans-5,11-dihydro-11-[(1,2-dimethyl-4-piperidinyl)acetyl]-6H-pyrido[2,3-b][1,4]benzodiazepin-6-one;
(f) cis-5,11-dihydro-11-[(1,3-dimethyl-4-piperidinyl)acetyl]-6H-pyrido[2,3-b][1,4]benzodiazepin-6-one;
(g) trans-5,11-dihydro-11-[(1,3-dimethyl-4-piperidinyl)acetyl]-6H-pyrido[2,3-b][1,4]benzodiazepin-6-one;
(h) 5,11-dihydro-11-[(1-methyl-1,2,5,6-tetrahydro-4-pyridinyl)-acetyl]-6H-pyrido[2,3-b][1,4]benzodiazepin-6-one;
(i) 5,11-dihydro-11-[(1,2-dimethyl-1,2,5,6-tetrahydro-4-pyridinyl)-acetyl]-6H-pyrido[2,3-b][1,4]benzodiazepin-6-one;
(j) 5,11-dihydro-11-[(1,3-dimethyl-1,2,5,6-tetrahydro-4-pyridinyl)-acetyl]-6H-pyrido[2,3-b][1,4]benzodiazepin-6-one;
(k) 5,11-dihydro-11-[(1,5-dimethyl-1,2,5,6-tetrahydro-4-pyridinyl)-acetyl]-6H-pyrido[2,3-b][1,4]benzodiazepin-6-one;
(l) 5,11-dihydro-11-[(1,6-dimethyl-1,2,5,6-tetrahydro-4-pyridinyl)-acetyl]-6H-pyrido[2,3-b][1,4]benzodiazepin-6-one;
(m) 5,11-dihydro-11-[(1,2,6-trimethyl-1,2,5,6-tetrahydro-4-pyridinyl)carbonyl]-6H-pyrido[2,3-b][1,4]benzodiazepin-6-one;
(n) cis-5,11-dihydro-4-[(1,2,6-trimethyl-1,2,5,6-tetrahydro-4-pyridinyl)carbonyl]-6H-pyrido[2,3-b][1,4]benzodiazepin-6-one;
(o) trans-5,11-dihydro-11-[(1,2,6-trimethyl-1,2,5,6-tetrahydro-4-pyridinyl)carbonyl]-6H-pyrido[2,3-b][1,4]benzodiazepin-6-one;
(p) 5,11-dihydro-11-[(1-methyl-1,2,5,6-tetrahydro-4-pyridinyl)-carbonyl]-6H-pyrido[2,3-b][1,4]benzodiazepin-6-one;
(q) 5,11-dihydro-11-[(1,2-dimethyl-1,2,5,6-tetrahydro-4-pyridinyl)-carbonyl]-6H-pyrido[2,3-b][1,4]benzodiazepin-6-one;
(r) 5,11-dihydro-11-[(1,3-dimethyl-1,2,5,6-tetrahydro-4-pyridinyl)-carbonyl]-6H-pyrido[2,3-b][1,4]benzodiazepin-6-one;
(s) 5,11-dihydro-11-[(1,5-dimethyl-1,2,5,6-tetrahydro-4-pyridinyl)-carbonyl]-6H-pyrido[2,3-b][1,4]benzodiazepin-6-one;
(t) 5,11-dihydro-11-[(1,6-dimethyl-1,2,5,6-tetrahydro-4-pyridinyl)-carbonyl]-6H-pyrido[2,3-b][1,4]benzodiazepin-6-one;
(u) endo-5,11-dihydro-11-[(8-methyl-8-azabicyclo[3.2.1]oct-3-yl)-acetyl]-6H-pyrido[2,3-b][1,4]benzodiazepin-6-one;
(v) exo-5,11-dihydro-11-[(8-methyl-8-azabicyclo[3.2.1]oct-3-yl)-acetyl]-6H-pyrido[2,3-b][1,4]benzodiazepin-6-one;
(w) 5,11-dihydro-11-[(2,3-dehydro-8-methyl-8-azabicyclo[3.2.1]oct-3-yl)-acetyl]-6H-pyrido[2,3-b][1,4]benzodiazepin-6-one; and (x) 5,11-dihydro-11-[(1-methyl-4-piperidinylidene)acetyl]-6H-pyrido[2,3-b][1,4]benzodiazepin-6-one.

The pyridobenzodiazepinones of Formula I and the acid addition salts thereof have valuable properties which make them commercially viable, and they are characterized in particular by an excellent protective effect on the stomach and intestines in warm-blooded animals. For example, they inhibit the formation of gastric ulcers. Moreover, they have a useful therapeutic range, due to their low toxicity and the absence of any significant side effects.

The excellent activity of the pharmacologically active compounds of Formula I and of their pharmaceutically acceptable, i.e., biologically acceptable, acid addition salts makes it possible to use them in both human and veterinary medicine, for the treatment and prophylaxis of diseases based upon disorders of the stomach or intestines. They may be used, for example, to treat acute and chronic gastric and duodenal ulcers, gastritis, and gastric hyperactivity in humans and animals.

For such treatment, the compounds of Formula I and their pharmacologically acceptable salts can be incorporated, optionally in combination with other active ingredients, in manner known per se, into the usual pharmaceutical preparations such as tablets, coated tablets, capsules, powders, infusions, suppositories, solutions, or suspensions. The daily dose for adults is from about 0.75 to 375 mg (from about 0.01 to 5 mg/kg), preferably from about 1.5 to 188 mg (from about 0.02 to 2.5 mg/kg), more particularly, from about 3.75 to 75.0 mg (from about 0.05 to 1.0 mg/kg), generally administered in the form of several, preferably from 1 to 3, individual doses to achieve the desired results. Dependent upon the type and body weight of the patient to be treated, on the type and severity of the disease, on the type of preparation and on the route of administration as well as on the period or interval over which the administration takes place, it may, however, be necessary to deviate from the above dosages. Thus, it may be sufficient in some cases to administer more or less than the above-mentioned amounts of active ingredient. The optimum dosage and route of administration of the active ingredients which are necessary in each case can easily be determined by one skilled in the art.

Thus, the invention further relates to pharmaceutical compositions containing the compounds of Formula I or pharmacologically acceptable salts thereof. Similarly, the invention relates to the use of the compounds according to the invention in the preparation of pharmaceutical compositions used in the treatment of the diseases mentioned above.

If the pyridobenzodiazepinones of Formula I and/or the pharmacologically acceptable acid addition salts thereof are to be used to treat the diseases mentioned above, the pharmaceutical preparations may also contain one or more pharmacologically active components, i.e., active ingredients, from other groups of medicaments. Examples of such other active ingredients include antacids, such as, aluminum hydroxide or magnesium aluminate; secretion-inhibitors such as H₂ blockers, for instance, cimetidine or ranitidine; gastric and intestinal therapeutic agents such as metoclopramide, bromoprid, or tiaprid; tranquilizers such as benzodiazepines, for instance, diazepam or oxazepam; spasmolytics such as bietamiverine or camylofine; anticholinergics such as oxyphencyclimine or phencarbamide; glucocorticoids such as prednisolone, fluocortolone, or betamethasone; non-steroidal antiphlogistic agents such as arylacetic acids, arylpropionic acids, heteroarylacetic acids, heteroarylpropionic acids, benzothiazine carboxamide dioxides, pyrazolidinediones, or quinazolinones, for instance, ibuprofen, naproxen, diclofenac, fenbufen, flurbiprofen, indomethacin, lonazolac, sudoxicam, piroxicam, phenylbutazone, bumadizon-calcium, or proquazone; and local anaesthetics such as tetracaine or procaine. Optionally, enzymes, viatmins, amino acids, or the like, may also be present.

Another aspect of the invention relates to processes for the preparation of pyridobenzodiazepinones of Formula I as well as the acid addition salts thereof. These compounds can be prepared as follows:

Method A

Compounds of Formula I can be prepared by reacting pyridobenzodiazepinones of the formula

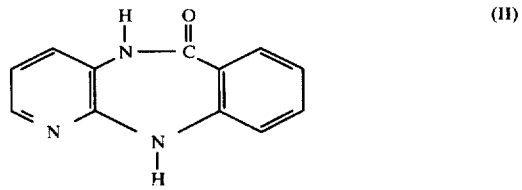

with acid derivatives of the formula

wherein R is as defined above and Z represents a nucleophobic group or a leaving group.

The reaction of the compounds of Formula II with the acid derivatives of Formula III is effected in a manner known per se. The leaving group Z is a group which, together with the carbonyl group to which it is bonded, forms a reactive carboxylic acid derivative. Examples of reactive carboxylic acid derivatives include acid halides, esters, anhydrides, and mixed anhydrides, as obtained from salts of the corresponding acid (Z=OH), and acid chlorides, such as phosphorus oxychloride, diphosphoric acid tetrachloride, or chloroformates, and the N-alkyl-2-acyloxypyridinium salts formed by reacting compounds of Formula III (Z=OH) with N-alkyl-2-halopyridinium salts.

The reaction is preferably carried out with the mixed anhydrides of strong inorganic acids, particularly dichlorophosphoric acid. The reaction is optionally carried out in the presence of an acid-binding agent (proton acceptor). Examples of suitable proton acceptors include alkali metal carbonates and alkali metal bicarbonates, such as sodium carbonate or potassium bicarbonate; tertiary organic amines, such as pyridine, triethylamine, ethyldiisopropylamine, or 4-dimethylaminopyridine; and sodium hydride. The reaction is carried out at temperatures of from about −25° to 130° C. in an inert solvent. Examples of suitable inert solvents include chlorinated aliphatic hydrocarbons such as methylene chloride or 1,2-dichloroethane; open-chained or cyclic ethers such as diethyl ether, tetrahydrofuran, or 1,4-dioxane; aromatic hydrocarbons such as benzene, toluene, xylene, or o-dichlorobenzene; polar aprotic solvents such as acetonitrile, dimethylformamide, or hexamethylphosphoric acid triamide; and mixtures thereof.

The reaction times are from about 15 minutes to 80 hours, dependent upon the quantity and nature of the acylation agent of Formula III used. It is not necessary to prepare the compounds of Formula III in pure form; instead, they may be produced in situ in the reaction mixture in known manner.

Method B

Compounds of Formula I wherein R represents (1-methyl-1,2,5,6-tetrahydro-4-pyridinyl)methyl or 1-methyl-1,2,5,6-tetrahydro-4-pyridinyl, optionally substituted by one or two methyl groups on the heterocyclic six-membered ring, can also be prepared by reacting, in a first step, a pyridobenzodiazepinone of Formula II with an acylation agent of the formula

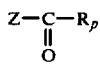
(IV)

wherein Z is as defined above for Formula III and $R_p$ represents an optionally methyl or dimethyl substituted 4-pyridinyl or (4-pyridinyl)methyl, to form an intermediate compound of the formula

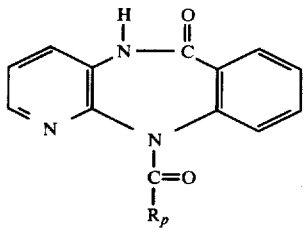
(V)

wherein $R_p$ is as defined above. Acylation will be successful under the conditions mentioned for Method A, but it is preferably to carry out the reaction in boiling dioxane in the presence of pyridine, 4-dimethylaminopyridine, or triethylamine.

The compounds of Formula V are then methylated with a methylation agent of the formula

(VI)

wherein X represents the acid group of a strong oxyacid, for example, of sulfuric, methylsulfuric, fluorosulfonic, trifluoromethanesulfonic, methanesulfonic, benzenesulfonic, p-toluenesulfonic, p-bromobenzenesulfonic, or phosphoric acid or a halide, preferably chloride, bromide, or iodide, to form a pyridinium salt of the formula

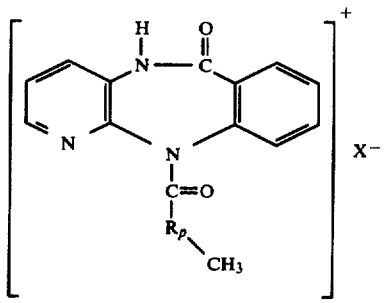
(Va)

wherein $R_p$ and X are as defined above. The methylation is carried out in inert solvent, e.g., a chlorinated aliphatic hydrocarbon, such as methylene chloride; 1,2-dichloroethane; an open-chained or cyclic ether, such as diethyl ether or tetrahydrofuran; or an aromatic hydrocarbon, such as benzene, toluene, xylene, or dichlorobenzene, but preferably in dioxane, acetonitrile, or dimethylformamide, and at temperatures of from about −20° to 130° C., preferably from about 30° to 100° C.

Subsequent reduction of the pyridinium salts of Formula Va with sodium or potassium borohydride or sodium or potassium alkoxyborohydride, dialkoxyborohydride, or trialkoxyborohydride in protic solvents, for example, in water, methanol, ethanol, 2-propanol, or mixtures thereof, at temperatures of from about −40° to 50° C., preferably at 0° C., produces the desired pyridobenzodiazepinones of Formula I wherein R represents (1-methyl-1,2,5,6-tetrahydro-4-pyridinyl)methyl or 1-methyl-1,2,5,6-tetrahydro-4-pyridinyl.

The processes for preparing the pharmacologically active pyridobenzodiazepinones of Formula I are thus characterized in that pyridobenzodiazepinones of Formula II are acylated with compounds of Formula III or with pyridine alkanoic acid derivatives of Formula IV, and then methylated and reduced with borohydrides or alkoxyborohydrides, and optionally the resulting base is subsequently converted into a pharmacologically acceptable acid addition salt or an acid addition salt obtained is converted into the free base or a pharmacologically acceptable acid addition salt using methods known per se.

Some of the pyridobenzodiazepinones of Formula I according to the invention contain one or two asymmetric carbon atoms in the R group. These compounds may therefore occur in two diastereomeric cis and trans forms or as the enantiomeric (+) and (−) forms. The invention includes the individual isomers and the mixtures thereof.

The diastereomers may be separated on the basis of their different physico-chemical properties, e.g., by fractional recrystallization from suitable solvents or by chromatographic methods. Only one diastereomer is obtained in Method A is carried out with only one diastereomer of Formula III.

Any racemates of the compounds of Formula I may be separated according to known methods, for example, by use of an optically active acid such as (+)- or (−)-tartaric acid or a derivative thereof, such as (+)- or (−)-diacetyl tartaric acid, (+)- or (−)-monomethyl tartrate, or (+)-camphorsulfonic acid.

In a conventional method for separating isomers, the racemate of a compound of Formula I is reacted with an equimolar quantity of one of the above-mentioned optically active acids in a solvent, and the crystalline optically active salts obtained are separated on the basis of their different solubilities. This reaction may be carried out in any type of solvent provided that the salts have sufficiently different solubilities therein. Preferably, methanol, ethanol, or a mixture thereof, for example, in proportions of 50:50 by volume, is used. Then, each of the optically active salts is dissolved in water and neutralized, and in this way the corresponding free compound is obtained in the (+) or (−) form.

Only one enantiomer is obtained when Method A is carried out with only one enantiomer of Formula III.

The 5,11-dihydro-6H-pyrido[2,3-b][1,4]benzodiazepin-6-one of Formula II required as a starting material is known from the literature. See, for example, U.S. Pat. No. 3,406,168, incorporated herein by reference.

Compounds of Formulae III and IV are known or may readily be obtained, as mentioned above, analogously to known methods of preparation. For example, by reaction of the sodium salt of 4-hydroxy-1-methyl-4-piperidino-acetic acid with thionyl chloride, a mixture of 1-methyl-1,2,5,6-tetrahydro-4-pyridinoacetic acid chloride and (1-methyl-4-piperidinylidene)acetyl chloride is obtained, which can be reacted according to Method A, without separation, with a pyridobenzodiazepine of Formula II to form a mixture of the desired compounds of Formula I wherein R represents (1-methyl-1,2,5,6-tetrahydro-4-pyridinyl)methyl and (1-methyl-4-piperidinylidene)methyl. Optionally this mixture of double bond isomers can subsequently be broken down into its components by a known method, for example, fractional crystallization, column chromatography, or high pressure liquid chromatography.

Moreover, tropan-3α-acetic acid and tropan-3β-acetic acid may each be obtained, free from the other isomer, using the method described by W. Schneider et al., Arch. Pharm. 308, 365–375 (1975), and Ch. L. Zirkle et al., J. Org. Chem. 27, 1279–1285 (1962). The reactive acid derivatives of these compounds may be, for example, the acid chlorides which may be prepared in the usual manner from the above-mentioned carboxylic acids by converting them into the potassium salt and subsequently treating the salt with purified thionyl chloride.

Optionally, methyl or dimethyl substituted 4-pyridinoacetic acids or isonicotinic acids are commercially available or may be synthesized analogously to or by means of an Arndt-Eistert reaction via the substituted isonicotinic acids described by D. Jerchel et al., Liebigs Ann. Chem. 613, 153–170 (1958), or by R. Lukes et al., Collect. Czechoslov. Chem. Commun. 23, 1083–1089 (1958); 27, 2220–2222 (1962). The reactive acid derivatives used may be, for example, the acid chloride hydrochlorides, which may be obtained according to or analogously to the method described by H. Leditschke, Arch. Pharm. 295, 328 (1962).

As already mentioned above, the novel compounds for Formula I have valuable pharmacological properties. In particular, they have anti-ulcerogenic effects, they inhibit gastric acid secretion, and they have favorable effects on various other disorders of the gastrointestinal tract, including, in particular, irritable colon.

A favorable relation between anti-ulcerogenic and antisecretory effects, on the one hand, and the undesirable effects on pupil size and the secretion of tears and saliva, on the other hand, which occurs particularly with therapeutic agents having an anti-cholinergic component, is of particular importance in the therapeutic use of the substances. The following tests show that the compounds according to the invention have surprisingly favorable characteristics in this respect.

1. Investigation of the selectivity of the antimuscarinic activity

Objects

Oxotremorine, a specific agonist for muscarinic receptors produces lesions in the mucous membrane of the stomach in rats and increases their secretion of saliva. This test method was chosen so that any selective activity of an antimuscarinic substance on the stomach could be identified.

Method

Ten female albino rats (of the Crl:COBS-CD (SD) BR strain) with a body weight of from 120 to 150 gm apiece were used in each treatment group and were kept without food for 24 hours before the start of the test but given free access to drinking water.

To determine, in preliminary tests, the muscarinic effect of oxotremorine on each of the symptoms studied, a dosage/activity curve was drawn up with at least three dosages for each symptom.

When the antimuscarinic substances were tested, the dosage of oxotremorine which triggered the symptom in question in 90 to 100% of the animals in the preliminary tests was used.

| Lesions in the mucous membrane of stomach | 0.62 mg/kg i.v. |
|---|---|
| Secretion of saliva | 0.083 mg/kg i.v. |

Each antimuscarinic substance was administered intravenously in uniformly graduated doses 15 minutes before the oxotremorine was administered. Control groups were given corresponding quantities of the solvent and suspension agent instead of the test substance. Immediately after the oxotremorine was administered, the animals were placed in a glass case for 15 minutes and observed.

The test for the effect on the oxotremorine-induced secretion of saliva was carried out as a blind test, i.e., the tester did not know which treatment the animals had been given.

The results were expressed as the percentage inhibition of the oxotremorine effect (the percentage of animals which did not show the symptom in question). The $ED_{50}$ values were determined using the method described by Litchfield and Wilcoxon (J. Pharmacol. Exp. Ther. 96, 99, 1949).

The effects on lesions of the mucous membrane of the stomach were evaluated as follows:

The lesions of the gastric mucous membrane were produced by intravenous injection of 0.62 mg/kg of oxotremorine 30 minutes after the oral administration of 1 mg/kg of neostigmine (a cholinesterase inhibitor). Sixty minutes after the administration of the neostigmine, the animals were killed, and the stomachs were removed, opened, and examined for the presence of any lesions in the mucous membrane. The protective effect of the test substances was expressed as the percentage inhibition (percentage of animals without lesions). The $ED_{50}$ and $ED_{70}$ values were determined using the method of LITCHFIELD and WILCOXON (see above).

2. Testing for mydriasis

The effect of the test substances on the pupil size in rats was investigated as follows:

The substances were administered intravenously to groups of 10 animals in at least three uniformly graduated doses. The pupil size was then observed for 10 minutes to see if there were any changes (mydriasis or miosis). Again, the test was carried out blind, i.e., the tester did not know what preliminary treatment the animals had received. The percentage of test animals in which mydriasis occurred was determined. The $ED_{50}$ values were again determined during the method of LITCHFIELD and WILCOXON (see above).

3. Studies of binding to muscarinic receptors:
Determination of the $IC_{50}$ value The organ donors were male Sprague-Dawley rats with a body weight of from about 180 to 220 gm each. After the heart, stomach, and cerebral cortex had been removed, the remainder of the operation was carried out in ice-cold Hepes-HCl buffer (pH 7.4; 100 m molar NaCl, 10 m molar $MgCl_2$). The smooth muscle of the fundus of the stomach was separated from the mucous membrane of the stomach and subjected to preliminary homogenization. The whole heart was cut up with scissors. All the organs were then homogenized in a Potter apparatus.

For the bonding test, the homogenized organs were diluted as follows:

| | |
|---|---|
| Smooth muscle of the fundus of the stomach | 1:100 |
| Whole heart | 1:250 |
| Cerebral cortex | 1:3000 |

The homogenized organ preparations were incubated at a specific concentration of the radioligand and with a series of concentrations of the non-radioactive test substances in an Eppendorf centrifuge tube at 30° C. The duration of incubation was 45 minutes. The substance 0.3 n molar $^3$H-N-methylscopolamine ($^3$H-NMS) was used as the radioligand. After incubation had been brought to an end by centrifuging at 14,000 g, the radioactivity in the pellet was determined. It represents the sum of the specific and non-specific binding of $^3$H-NMS. The proportion of non-specific bonding was defined as the radioactivity which was bonded in the presence of $1\mu$ molar quinuclidinylbenzylate. Four measurements were taken in each case. The $IC_{50}$ values of the non-labelled test substances were determined graphically. They represent the concentration of test substances at which the specific binding of $^3$H-NMS to the muscarinic receptors in the various organs was inhibited by 50%.

The following compounds, examples of compounds of Formula I, were tested as described above:

A = 5,11-dihydro-11-[(1-methyl-1,2,5,6-tetrahydro-4-pyridinyl)acetyl]-6H-pyrido[2,3-b][1,4]benzodiazepin-6-one and B = endo-5,11-dihydro-11-[(8-methyl-8-azabicyclo[3.2.1]oct-3-yl)acetyl]-6H-pyrido[2,3-b][1,4]benzodiazepin-6-one.

The testing results are set forth in the following table:

TABLE

| Substance | Receptor Binding Tests $IC_{50}$ [n mol $1^{-1}$] | | | Oxotremorine Test [μg/kg] i.v. | | | Mydriasis $ED_{50}$ [μg/kg] i.v. |
|---|---|---|---|---|---|---|---|
| | | Smooth Muscle | | Anti-ulcerative Effect | | Inhibition of Salivation | |
| | Cortex | Fundus of Stomach | Heart | $ED_{50}$ | $ED_{70}$ | $ED_{50}$ | |
| A | 50 | 200 | 170 | 1.1 | 2 | 28 | 74 |
| B | 50 | 700 | 150 | — | 37 | 300 | 220 |

The results in the above table show that the compounds mentioned generally have a high affinity with muscarinic receptors. Moreover, the results show that the novel compounds of Formula I differentiate between muscarinic receptors in different types of tissue. This is clear from the considerably lower $IC_{50}$ values in the tests on preparations from the cerebral cortex compared with those of the smooth muscle of the stomach and heart.

The pharmacological data in the above tabel show—in complete agreement with the receptor bonding studies—that the formation of oxotremorine-induced lesions in the mucous membrane of the stomach is inhibited by the above-mentioned compounds even at doses at which no restriction of salivation and no mydriasis can be observed.

The following examples are intended to illustrate the invention and should not be construed as limiting the invention thereto. In the examples, "M.p." or "m.p." indicates "melting point" and "D" indicates "decomposition".

EXAMPLES

EXAMPLE 1

5,11-Dihydro-11-[(1-methyl-1,2,5,6-tetrahydro-4-pyridinyl)acetyl]-6H-pyrido[2,3-b][1,4]benzodiazepin-6-one With external cooling and with a reaction temperature of 15° C. being maintained, 9.5 gm (0.08 mol) of thionyl chloride, dissolved in 20 ml of chloroform, were added dropwise to a suspension of 14.0 gm (0.072 mol) of the potassium salt of 1-methyl-1,2,5,6-tetrahydro-4-pyridinoacetic acid in 150 ml of anhydrous chloroform. The mixture was stirred for a 20 minutes and then concentrated to dryness by evaporation in vacuo. The residue remaining was added to a suspension of 8.4 gm (0.04 mol) of 5,11-dihydro-6H-pyrido[2,3-b][1,4]benzodiazepin-6-one in a mixture of solvents consisting of 300 ml of absolute dioxane and 20 ml of anhydrous pyridine. The mixture was heated to 80° C. for two hours under vigorous stirring. After cooling, it was filtered, and the filter residue was taken up in water. This was then made alkaline with solid sodium carbonate, and the aqueous phase was exhaustively extracted with chloroform. The combined chloroform extracts were dried, and the solvent was eliminated in vacuo. The residue was purified by column chromatography on aluminium oxide (activity stage I), a mixture of ethyl acetate and methanol (volume ratio of 4:1) being used as eluant. After trituration with ethyl acetate, 1.5 gm (11% of theory) of colorless crystals were obtained, m.p.: 200°-202° C. (D).

By use of analogous procedures, the following compounds were prepared:

(a) endo-5,11-dihydro-11-[(8-methyl-8-azabicyclo[3.2.1]oct-3-yl)acetyl]-6H-pyrido[2,3-b][1,4]benzodiazepin-6-one, M.p.: 239°-240° C.;

(b) exo-5,11-dihydro-11-[(8-methyl-8-azabicyclo[3.2.1]oct-3-yl)-acetyl]-6H-pyrido[2,3-b][1,4]benzodiazepin-6-one; and (c) 5,11-dihydro-11-[(2,3-dehydro-8-methyl-8-azabicyclo[3.2.1]oct-3-yl)-acetyl]-6H-pyrido[2,3-b][1,4]benzodiazepin-6-one, R$_f$: 0.47 [methylene chloride/cyclohexane/methanol/ammonia (68:15:15:2)].

EXAMPLE 2

5,11-Dihydro-11-[(1-methyl-1,2,5,6-tetrahydro-4-pyridinyl)acetyl]-6H-pyrido[2,3-b][1,4]benzodiazepin-6-one and 5,11-Dihydro-11-[(1-methyl-4-piperidinylidene)acetyl]-6H-pyrido[2,3-b][1,4]benzodiazepin-6-one To a suspension of 16.8 gm (0.08 mol) of the potassium salt of 4-hydroxy-1-methyl-4-piperidinoacetic acid in 300 ml of chloroform, a solution of 14.2 gm (0.12 mol) of thionyl chloride in 50 ml of chloroform was added dropwise, with external cooling, while a reaction temperature of 15° C. was maintained. After the mixture had been stirred for 20 minutes, it was concentrated by evaporation in vacuo, and the residue was then added to a suspension of 8.4 gm (0.04 mol) of 5,11-dihydro-6H-pyrido[2,3-b][1,4]benzodiazepin-6-one in a mixture of 400 ml of anhydrous dioxane and 20 ml of dry pyridine. The mixture was refluxed for two hours, under vigorous stirring. After the mixture cooled, the precipitate was filtered off and taken up in water. The aqueous solution was made alkaline with solid sodium carbonate and then exhaustively extracted with chloroform. The combined extracts were dried and concentrated by evaporation in vacuo, and the residue was then purified by column chromatography on aluminium oxide (activity stage 1) ethyl acetate/methanol (volume ratio of 99:1) being used as eluant. Quantities of 2.5 gm (18% of theory) of 5,11-dihydro-11-[(1-methyl-1,2,5,6-tetrahydro-4-pyridinyl)acetyl]-6H-pyrido[2,3-b][1,4]benzodiazepin-6-one, which, according to thin layer chromatography and IR and NMR spectra, was absolutely identical to a product prepared according to Example 1, and 0.3 gm (2.2% of theory) of 5,11-dihydro-11-[(1-methyl-4-piperidinylene)acetyl]-6H-pyrido[2,3-b][1,4]benzodiazepin-6-one, were obtained.

EXAMPLE 3 endo-5,11-Dihydro-11-[(8-methyl-8-azabicyclo[3.2.1]oct-3-yl)acetyl]-6H-pyrido[2,3-b][1,4]benzodiazepin-6-one The above compound was prepared analogously to Example 1 from the potassium salt of tropan-3α-acetic acid and 5,11-dihydro-6H-pyrido[2,3-b][1,4]benzodiazepin-6-one, in a yield of 37% of theory.

M.p.: 239°–240° C.

EXAMPLE 4

5,11-Dihydro-11-[(1-methyl-4-piperidinyl)acetyl]-6H-pyrido[2,3-b][1,4]benzodiazepin-6-one The above compound was prepared analogously to Example 1 from the potassium salt of 1-methyl-4-piperidinoacetic acid and 5,11-dihydro-6H-pyrido[2,3-b][1,4]benzodiazepin-6-one in a yield of 23% of theory.

Wax-like substance, m.p.: >95° C.

$C_{20}H_{22}N_4O_2$ (350.42); Calculated: C: 68.55, H: 6.33, N: 15.99, Found: C: 68.00 H: 6.51 N: 15.37.

MS: (m/e)=350 (311; 140; 96).

IR (CH$_2$Cl$_2$): NH 3370/cm; CO 1670/cm, 1680/cm.

UV (ethanol): λmax 300 nm (E=0.14).

UV (ethanol/KOH): λmax 250 nm (E=0.12); (c=50 mg/l; layer thickness d=2 mm).

$^1$N-NMR (CDCl$_3$/D$_2$O; 80 MHz): δ=8.23 (1H—dd; J=5.3 and 1.8 Hz; 2—H); 7.91 Hz (1H—dd; J=7.5 and 1.4 Hz; 4—H); 7.1–7.7 (6H—m; ar.H); 2.5–2.9 (2H—m); 0.8–2.4 (12H—m), then at δ=2.18 (3H—s; N—CH$_3$).

By use of analogous procedures, the following compounds were prepared:
(a) 5,11-dihydro-11-[(1,3-dimethyl-4-piperidinyl)acetyl]-6H-pyrido[2,3-b][1,4]benzodiazepin-6-one;
(b) 5,11-dihydro-4-[(1,2-dimethyl-4-piperidinyl)acetyl]-6H-pyrido[2,3-b][1,4]benzodiazepin-6-one; and
(c) exo-5,11-dihydro-11-[(8-methyl-8-azabicyclo[3.2.1]oct-3-yl)-acetyl]-6H-pyrido[2,3-b][1,4]benzodiazepin-6-one.

EXAMPLE 5

5,11-Dihydro-11-[(1-methyl-1,2,5,6-tetrahydro-4-pyridinyl)carbonyl]-6H-pyrido[2,3-b][1,4]benzodiazepin-6-one A mixture of 10.6 gm (0.05 mol) of 5,11-dihydro-6H-pyrido[2,3-b][1,4]benzodiazepin-6-one, 10.8 gm (0.055 mol) of 1-methyl-1,2,5,6-tetrahydroisonicotinic acid chloride hydrochloride, 20.7 gm (0.15 mol) of potassium carbonate, and 200 ml of anhydrous toluene was refluxed for 48 hours under thorough stirring. After the mixture cooled, it was stirred into 500 ml of ice water, the organic layer was separated off, and the aqueous layer was exhaustively extracted with ethyl acetate. The combined organic phases were dried over sodium sulphate and then concentrated by evaporation in vacuo. The residue was purified by column chromatography, first on silica gel with a particle size of from 0.1 to 0.4 mm, 1,2-dichloroethane/methanol (volume ratio of 9:1) being used as eluant, and secondly on silica gel with a particle size of from 0.032 to 0.063 mm, methylene chloride/methanol (volume ratio of 10:1) being used as eluant. The appropriate fractions were worked up in the usual way to produce colorless crystals, m.p.: 226°–227° C. (diisopropylether/methanol). Yield: 210 mg (1.3% of theory).

EXAMPLE 6

5,11-Dihydro-11-[1-methyl-1,2,5,6-tetrahydro-4-pyridinyl)carbonyl]-6H-pyrido[2,3-b][1,4]benzodiazepin-6-one (a)

5,11-Dihydro-11-[(4-pyridinyl)carbonyl]-6H-pyrido[2,3-b][1,4]benzodiazepin-6-one A mixture of 40.4 gm (0.191 mol) of 5,11-dihydro-6H-pyrido[2,3-b][1,4]benzodiazepin-6-one, 46.0 gm (0.258 mol) of isonicotinic acid chloride hydrochloride, 42 ml (0.52 mol) of pyridine, and 600 ml of anhydrous dioxane was refluxed for three hours. After cooling, the mixture was filtered, the filter residue was taken up in 300 ml of water, and the solution obtained was extracted twice, each time with 100 ml of dichloromethane. The aqueous phase was made alkaline with sodium hydroxide solution and exhaustively extracted with methylene chloride. The methylene chloride extracts thus obtained were washed with water and dried over sodium sulphate, and the solvent was eliminated in vacuo. The residue was recrystallized from hot methanol. After washing with ether, the resulting beige-colored crystals melted at 265°–266° C.

Yield: 21.0 gm (35% of theory).

(b)

5,11-Dihydro-11-[(4-pyridinyl)carbonyl]-6H-pyrido[2,3-b][1,4]benzodiazepin-6-one methoiodide An amount of 6.3 gm (0.02 mol) of 5,11-dihydro-11-[(4-pyridinyl)carbonyl]-6H-pyrido[2,3-b][1,4]benzodiazepin-6-one was dissolved in 100 ml of anhydrous dimethylformamide, and, after addition of 3.2 gm (0.0227 mol) of iodomethane, the mixture was stirred at ambient temperature overnight. It was then concentrated by evaporation in vacuo to one-third of its original volume, after which a mixture of equal parts by volume of methanol and ether was added thereto until the salt formed began to crystallize out. After being left to stand for two hours at ambient temperature, the mixture was subjected to suction filtration, and the precipitate was thoroughly washed with ether. Yellow crystals, in an amount of 7.2 gm (78% of theory), were obtained, m.p.: 290° C. (D).

(c)
5,11-Dihydro-11-[(1-methyl-1,2,5,6-tetrahydro-4-pyridinyl)carbonyl]-6H-pyrido[2,3-b][1,4]benzodiazepin-6-one A quantity of 2.3 gm (0.005 mol) of 5,11-dihydro-11-[(4-pyridinyl)-carbonyl]-6H-pyrido[2,3-b][1,4]benzodiazepin-6-one methoiodide was suspended in 200 ml of methanol, and at 0° C. 0.25 gm (0.006 mol) of sodium borohydride were added thereto in portions. The resulting mixture was stirred for a further hour in an ice bath. Then, the mixture was stirred into 1 liter of ice-cold water and extracted exhaustively with methylene chloride. The combined extracts were washed with water, dried over sodium sulphate, and concentrated by evaporation in vacuo. After being recrystallized from diisopropyl ether/methanol, the colorless crystals melted at 226°-227° C.

Yield: 0.9 gm (54% of theory).

According to thin layer chromatography and IR and NMR spectra, the product was identical to a product prepared according to Example 5.

By use of analogous procedures, the following compounds were prepared:

(a) 5,11-dihydro-11-[(1,2,6-trimethyl-1,2,5,6-tetrahydro-4-pyridinyl)carbonyl]-6H-pyrido[2,3-b][1,4]benzodiazepin-6-one;

(b) 5,11-dihydro-11-[(1,3-dimethyl-1,2,5,6-tetrahydro-4-pyridinyl)carbonyl]-6H-pyrido[2,3-b][1,4]benzodiazepin-6-one and 5,11-dihydro-11-[(1,5-dimethyl-1,2,5,6-tetrahydro-4-pyridinyl)carbonyl]-6H-pyrido[2,3-b][1,4]benzodiazepin-6-one,
prepared by reacting 5,11-dihydro-6H-pyrido[2,3-b][1,4]benzodiazepin-6-one with 3-methylisonicotinic acid chloride hydrochloride (m.p.: 155°-156° C.), via
5,11-dihydro-11-[(3-methyl-4-pyridinyl)carbonyl]-6H-pyrido[2,3-b][1,4]benzodiazepin-6-one and
5,11-dihydro-11-[(3-methyl-4-pyridinyl)carbonyl]-6H-pyrido[2,3-b][1,4]benzodiazepin-6-one methoiodide;

(c) 5,11-dihydro-11-[(1,2-dimethyl-1,2,5,6-tetrahydro-4-pyridinyl)carbonyl]-6H-pyrido[2,3-b][1,4]benzodiazepin-6-one and 5,11-dihydro-11-[(1,6-dimethyl-1,2,5,6-tetrahydro-4-pyridinyl)carbonyl]-6H-pyrido[2,3-b][1,4]benzodiazepin-6-one,
prepared by reacting 5,11-dihydro-6H-pyrido[2,3-b][1,4]benzodiazepin-6-one with 2-methylisonicotinic acid chloride hydrochloride, via
5,11-dihydro-11-[2-methyl-4-pyridinyl)carbonyl]-6H-pyrido[2,3-b][1,4]benzodiazepin-6-one and
5,11-dihydro-11-[(2-methyl-4-pyridinyl)carbonyl]-6H-pyrido[2,3-b][1,4]benzodiazepin-6-one methoiodide; and (d) 5,11-dihydro-11-[(1-methyl-1,2,5,6-tetrahydro-4-pyridinyl)acetyl]-6H-pyrido[2,3-b][1,4]benzodiazepin-6-one,
prepared by reacting 5,11-dihydro-6H-pyrido[2,3-b][1,4]benzodiazepin-6-one with 4-pyridinoacetic acid chloride hydrochloride, via
5,11-dihydro-11-[(4-pyridinyl)acetyl]-6H-pyrido[2,3-b][1,4]benzodiazepin-6-one and
5,11-dihydro-11-[(4-pyridinyl)acetyl]-6H-pyrido[2,3-b][1,4]benzodiazepin-6-one methoiodide.

EXAMPLE 7

5,11-Dihydro-11-[(1-methyl-1,2,5,6-tetrahydro-4-pyridinyl)acetyl]-6H-pyrido[2,3-b][1,4]benzodiazepin-6-one A mixture of 0.97 gm (6.25 mol) of 1-methyl-1,2,5,6-tetrahydro-4-pyridinoacetic acid and 0.20 gm (6.25 mmol) of 75% sodium hydride (in paraffin oil) in 16 ml of dimethylformamide was heated to 50°-80° C. until the development of hydrogen ceased (2 to 3 hours). To the sodium salt of the acid thus obtained, 1.318 gm (6.24 mmol) of 5,11-dihydro-6H-pyrido[2,3-b][1,4]benzodiazepin-6-one were added, and, at −10° C., 0.99 gm of 98% phosphorus oxytrichloride were added thereto dropwise over a period of 10 minutes. The mixture was stirred for four hours at −10° C., for four hours at 0° C., and for twenty hours at ambient temperature. The mixture was stirred into 200 gm of crushed ice, adjusted to a pH of 3.5 with sodium hydroxide solution, and extracted once with methylene chloride. Then, the aqueous phase was adusted to a pH of 9 and exhaustively extracted with methylene chloride. The organic phase was washed with water, dried over sodium sulphate, and concentrated by evaporation in vacuo. After purification by column chromatography on silica gel (eluant: ethyl acetate/methanol in a volume ratio of 9:1), 0.58 gm (27% of theory) of a colorless product were obtained, which product melted at 201°-202° C. (D) after recrystallization from ethyl acetate. The product was identical—according to thin layer chromatography, elementary analysis, and IR spectrum—to a product prepared according to Example 1.

By use of analogous procedures, the following compounds were prepared:

(a) endo-5,11-dihydro-11-[(8-methyl-8-azabicyclo[3.2.1]oct-3-yl)-acetyl]-6H-pyrido[2,3-b][1,4]benzodiazepin-6-one,
M.p.: 239°-240° C.;

(b) exo-5,11-dihydro-11-[(8-methyl-8-azabicyclo[3.2.1]oct-3-yl)-acetyl]-6H-pyrido[2,3-b][1,4]benzodiazepin-6-one;

(c) 5,11-dihydro-11-[(1-methyl-4-piperidinyl)acetyl]-6H-pyrido[2,3-b][1,4]benzodiazepin-6-one, identical, according to thin layer chromatography and IR and $^1$H-NMR spectra, to a product prepared according to Example 4; and (d) 5,11-dihydro-11-[(1-methyl-1,2,5,6-tetrahydro-4-pyridinyl)-carbonyl]-6H-pyrido[2,3-b][1,4]benzodiazepin-6-one,
M.p.: 226°-227° C. (diisopropylether/methanol).

EXAMPLE 8

5,11-Dihydro-11-[(1-methyl-1,2,5,6-tetrahydro-4-pyridinyl)acetyl]-6H-pyrido[2,3-b][1,4]benzodiazepin-6-one To a suspension of 1.552 gm (10 mmol) of 1-methyl-1,2,5,6-tetrahydro-4-pyridinoacetic acid in 20 ml of anhydrous tetrahydrofuran, 1.1 gm (10.14 mmol) of ethyl chlorocarbonate were added dropwise at 0° C. An amount of 2.11 gm (10 mmol) of 5,11-dihydro-6H- pyrido[2,3-b][1,4]benzodiazepin-6-one was added to the resulting mixture, which was stirred for a further hour at 0° C. and then for 4 hours at ambient temperature. Afterwards, the mixture was stirred into 160 ml of 2 N sodium hydroxide solution, while being externally cooled with ice. The resulting mixture was exhaustively extracted with dichloromethane, and the organic phase was concentrated to dryness by evaporation in vacuo. After purification by column chromatography on silica gel (eluant: ethyl acetate/methanol in a volume ratio of 9:1), 0.65 gm (19% of theory) of a colorless product was obtained, which product melted at 201°-202° C. after being recrystallized from ethyl acetate. According to thin layer chromatography and IR and NMR spectra, the product was absolutely identical to a product synthesized according to Example 1.

By use of analogous procedures, the following compounds were prepared:

(a) 5,11-dihydro-11-[(1-methyl-1,2,5,6-tetrahydro-4-pyridinyl)-carbonyl]-6H-pyrido[2,3-b][1,4]benzodiazepin-6-one, m.p.: 226°-227° C. (diisopropylether/methanol), prepared from 5,11-dihydro-6H-pyrido[2,3-b][1,4]benzodiazepin-6-one and 1-methyl-1,2,5,6-tetrahydro-isonicotinic acid;

(b) endo-5,11-dihydro-11-[(8-methyl-8-azabicyclo[3.2.1]oct-3-yl)-acetyl]-6H-pyrido[2,3-b][1,4]benzodiazepin-6-one, m.p.: 239°-240° C., prepared from 5,11-dihydro-6H-pyrido[2,3-b][1,4]benzodiazepin-6-one and tropan-3α-acetic acid; and (c) 5,11-dihydro-11-[(1-methyl-4-piperidinyl)acetyl]-6H-pyrido[2,3-b][1,4]benzodiazepin-6-one, which was identical—according to thin layer chromatography and IR and $^1$H-NMR spectra—to a product prepared according to Example 1, prepared from 5,11-dihydro-6H-pyrido[2,3-b][1,4]benzodiazepin-6-one and 1-methyl-4-piperidinoacetic acid.

The following examples are illustrative of a few pharmaceutical dosage unit compositions comprising a compound of the invention, namely, 5,11-dihydro-11-[(1-methyl-1,2,5,6-tetrahydro-4-pyridinyl)-acetyl]-6H-pyrido[2,3-b][1,4]benzodiazepin-6-one, as active ingredient.

EXAMPLE 9

Tablets containing 5 mg of active ingredient

Each tablet is compounded from the following ingredients:

| Component | Amount (mg) |
| --- | --- |
| Active ingredient | 5.0 |
| Lactose | 148.0 |
| Potato starch | 65.0 |
| Magnesium stearate | 2.0 |
| TOTAL | 220.0 |

Preparation

A 10% mucilage is prepared from potato starch by heating. The active ingredient, lactose, and remaining potato starch are mixed together and granulated with the mucilage through a screen with a mesh size of 1.5 mm. The granulate is dried at 45° C., passed through the screen again, mixed with magnesium stearate, and compressed to form tablets.

| Weight of tablet | 220 mg |
| --- | --- |
| Punch | 9 mm |

EXAMPLE 10

Coated tablets containing 5 mg of active ingredient

The tablets prepared according to Example 9 are coated by a known method with a shell consisting essentially of sugar and talc. The finished coated tablets are polished with beeswax.
Weight of coated tablet: 300 mg.

EXAMPLE 11

Ampules containing 1 mg of active ingredient

Each ampule contains a solution having the following composition:

| Component | Amount |
| --- | --- |
| Active ingredient | 1.0 mg |
| Sodium chloride | 8.0 mg |
| Distilled water | q.s. ad 1 ml |

Preparation

The active ingredient and sodium chloride are dissolved in distilled water and then topped up to the volume given. The solution is sterilized by filtration and transferred into 1 ml ampules.
Sterilization: 20 minutes at 120° C.

EXAMPLE 12

Suppositories containing 5 mg of active ingredient

Each suppository has the following composition:

| Component | Amount (mg) |
| --- | --- |
| Active ingredient | 5.0 |
| Suppository mass (e.g., WITEPSOL ® W 45, available from Chemische Werke Witten GmbH). | 1 695.0 |
| TOTAL | 1 700.0 |

Preparation

The finely powdered active ingredient is suspended in the molten suppository mass, which has been cooled to 40° C. At 37° C. the mass is poured into slightly chilled suppository molds.
Weight of suppository: 1.7 gm.

EXAMPLE 13

Drops containing 5 mg/ml of active ingredient

One hundred milliliters of drop solution have the following composition:

| Component | Amount |
| --- | --- |
| Active ingredient | 0.5 gm |
| Methyl p-hydroxybenzoate | 0.035 gm |
| Propyl p-hydroxybenzoate | 0.015 gm |
| Anise oil | 0.5 gm |
| Menthol | 0.06 gm |
| Pure ethanol | 10.0 gm |
| Sodium cyclamate | 1.0 gm |
| Glycerol | 15.0 gm |

| Component | Amount |
| --- | --- |
| Distilled water | q.s. ad 100.0 ml |

Preparation

The active ingredient and sodium cyclamate are dissolved in about 70 ml of water, and glycerol is added thereto. The p-hydroxybenzoates, anise oil, and menthol are dissolved in the ethanol, and this solution is added to the aqueous solution, under stirring. Finally, the mixture is made up to 100 ml with water and filtered to remove any suspended particles.

Any one of the other compounds embraced by Formula I, or a combination thereof, may be substituted for the particular active ingredient employed in Examples 9 through 13. Likewise, the amount of active ingredient in these illustrative examples may be varied to achieve the dosage unit range set forth above, and the amounts and nature of the inert pharmaceutical carrier ingredient may be varied to meet particular requirements.

While the present invention has been illustrated with the aid of certain specific embodiments thereof, it will be readily apparent to others skilled in the art that the invention is not limited to these particular embodiments, and the various changes and modifications may be made without departing from the spirit of the invention or the scope of the appended claims.

We claim:

1. A compound of the formula

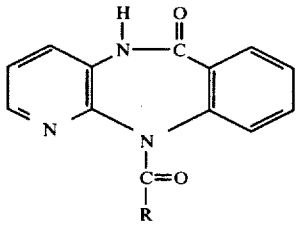

(I)

wherein R is (1-methyl-4-piperidinyl)methyl, (1-methyl-1,2,5,6-tetrahydro-4-pyridinyl)methyl, 1-methyl-1,2,5,6-tetrahydro-4-pyridinyl, (1-methyl-4-piperidinylidene)-methyl, 2,3-dehydro-8-methyl-8-azabicyclo[3.2.1]oct-3-yl-methyl group, or endo or exo-8-methyl-8-azabicyclo[3.2.1]oct-3-yl-methyl, each of which may optionally have one or two methyl substituents on the six-membered heterocyclic ring, a diastereomer or entaniomer thereof, or a non-toxic, pharmacologically acceptable acid addition salt thereof with an inorganic or organic acid.

2. A compound of claim 1, wherein R is (1-methyl-4-piperidinyl)methyl, 1-methyl-1,2,5,6-tetrahydro-4-pyridinyl, or endo-8-methyl-8-azabicyclo[3.2.1]oct-3-yl-methyl, or a non-toxic, pharmacologically acceptable acid addition salt thereof with an inorganic or organic acid.

3. 5,11-Dihydro-11-[(1-methyl-1,2,5,6-tetrahydro-4-pyridinyl)-acetyl]-6H-pyrido[2,3-b][1,4]benzodiazepin-6-one or a non-toxic, pharmacologically acceptable acid addition salt thereof.

4. endo-5,11-dihydro-11-[(8-methyl-8-azabicyclo[3.2.1]oct-3-yl)-acetyl]-6H-pyrido[2,3-b][1,4]benzodiazepin-6-one or a non-toxic, pharmacologically acceptable salt thereof.

5. An anti-ulcerogenic pharmaceutical composition consisting essentially of an inert pharmaceutical carrier and an effective anti-ulcerogenic amount of a compound of claim 1.

6. The method of inhibiting the formation of gastric ulcers is a warm-blooded animal in need thereof, which comprises perorally, parenterally, or rectally administering to said animal an effective anti-ulcerogenic amount of a compound of claim 1.

* * * * *

UNITED STATES PATENT AND TRADEMARK OFFICE
CERTIFICATE OF CORRECTION

PATENT NO. : 4,424,226
DATED : January 3, 1984
INVENTOR(S) : WOLFGANG EBERLEIN et al.

It is certified that error appears in the above-identified patent and that said Letters Patent are hereby corrected as shown below:

Column 10, line 3, "tabel" should read -- table --.

Column 11, line 60, "311" should read -- 211 --.

Column 18, line 2 of Claim 6, "is" should read -- in --.

Signed and Sealed this

Nineteenth Day of June 1984

[SEAL]

Attest:

Attesting Officer

GERALD J. MOSSINGHOFF

Commissioner of Patents and Trademarks